United States Patent
Guarr et al.

(10) Patent No.: US 11,094,964 B2
(45) Date of Patent: Aug. 17, 2021

(54) RECHARGEABLE ELECTROCHEMICAL CELL

(71) Applicant: Board of Trustees of Michigan State University, East Lansing, MI (US)

(72) Inventors: Thomas F. Guarr, Holland, MI (US); Daniel R. Henton, Midland, MI (US); Amber Prins, Holland, MI (US); Adina Dumitrascu, Midland, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 69 days.

(21) Appl. No.: 16/462,419

(22) PCT Filed: Nov. 21, 2017

(86) PCT No.: PCT/US2017/062698
§ 371 (c)(1),
(2) Date: May 20, 2019

(87) PCT Pub. No.: WO2018/098116
PCT Pub. Date: May 31, 2018

(65) Prior Publication Data
US 2019/0372163 A1    Dec. 5, 2019

Related U.S. Application Data

(60) Provisional application No. 62/425,226, filed on Nov. 22, 2016.

(51) Int. Cl.
| | | |
|---|---|---|
| *H01M 10/0567* | (2010.01) | |
| *H01M 10/0525* | (2010.01) | |
| *H01M 10/42* | (2006.01) | |
| *H01M 8/18* | (2006.01) | |
| *C07D 279/34* | (2006.01) | |
| *H01G 11/02* | (2013.01) | |
| *H01G 11/16* | (2013.01) | |
| *H01G 11/60* | (2013.01) | |
| *H01G 11/62* | (2013.01) | |
| *H01G 11/64* | (2013.01) | |

(52) U.S. Cl.
CPC ...... *H01M 10/0567* (2013.01); *C07D 279/34* (2013.01); *H01G 11/02* (2013.01); *H01G 11/16* (2013.01); *H01G 11/60* (2013.01); *H01G 11/62* (2013.01); *H01G 11/64* (2013.01); *H01M 8/188* (2013.01); *H01M 10/0525* (2013.01); *H01M 10/4235* (2013.01); *H01M 2300/0025* (2013.01)

(58) Field of Classification Search
CPC .......... H01M 10/052; H01M 10/0525; H01M 10/0567; H01M 10/4235; H01M 2300/0025; H01M 8/188
See application file for complete search history.

(56) References Cited

U.S. PATENT DOCUMENTS

| | | |
|---|---|---|
| 3,896,145 A | 7/1975 | Berger et al. |
| 5,976,731 A | 11/1999 | Negoro et al. |
| 6,249,369 B1 | 6/2001 | Theiste et al. |
| 6,445,486 B1 | 9/2002 | Lomprey et al. |
| 7,615,312 B2 | 11/2009 | Dahn et al. |
| 7,615,317 B2 | 11/2009 | Dahn et al. |
| 7,811,710 B2 | 10/2010 | Dahn et al. |
| 7,851,092 B2 | 12/2010 | Amine et al. |
| 8,367,253 B2 | 2/2013 | Chen et al. |
| 8,384,068 B2 | 2/2013 | Kahle et al. |
| 8,609,287 B2 | 12/2013 | Zhang et al. |
| 9,209,476 B2 | 12/2015 | Knuckey et al. |
| 2005/0221196 A1 | 10/2005 | Dahn et al. |
| 2006/0257746 A1 | 11/2006 | Inagaki et al. |
| 2006/0263697 A1 | 11/2006 | Dahn et al. |
| 2007/0020479 A1 | 1/2007 | Uetani et al. |
| 2007/0196727 A1 | 8/2007 | Wang et al. |
| 2008/0014496 A1 | 1/2008 | Watanabe et al. |
| 2009/0042103 A1 | 2/2009 | Xiao et al. |
| 2010/0068621 A1 | 3/2010 | Exnar et al. |
| 2010/0187980 A1 | 7/2010 | Langer et al. |
| 2010/0297480 A1 | 11/2010 | Martinent et al. |
| 2011/0006738 A1 | 1/2011 | Mikhaylik et al. |
| 2011/0079773 A1 | 4/2011 | Wasielewski et al. |
| 2011/0244319 A1 | 10/2011 | Hashimoto |
| 2011/0294019 A1 | 12/2011 | Amine et al. |
| 2013/0288137 A1 | 10/2013 | Weng et al. |
| 2014/0178756 A1* | 6/2014 | Ishii .............. H01M 4/13 429/211 |
| 2015/0108451 A1 | 4/2015 | Thompson et al. |

(Continued)

FOREIGN PATENT DOCUMENTS

| | | |
|---|---|---|
| CN | 101595591 A | 12/2009 |
| EP | 0 827 230 A2 | 3/1998 |
| FR | 2866478 A1 | 8/2005 |
| GB | 2507661 A | 5/2014 |
| JP | H08195199 A | 7/1996 |

(Continued)

OTHER PUBLICATIONS

R. L. Wang and J. R. Dahn. Computational Estimates of Stability of Redox Shuttle Additives for Li-Ion Cells, 2006 J. Electrochem. Soc. 153 A1922.*

Examination Report No. 1 (AU Application No. 2018302335); dated Apr. 24, 2020; 9 pages.

(Continued)

*Primary Examiner* — Carlos Barcena
(74) *Attorney, Agent, or Firm* — Howard & Howard Attorneys PLLC

(57) ABSTRACT

A rechargeable electrochemical cell includes a positive electrode having a recharged potential, a negative electrode, and a charge-carrying electrolyte. The rechargeable electrochemical cell further includes an active material having the following structure. (I)

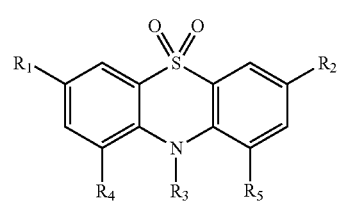

(I)

19 Claims, No Drawings

(56) References Cited

U.S. PATENT DOCUMENTS

| | | | |
|---|---|---|---|
| 2015/0248969 | A1 | 9/2015 | Watanabe et al. |
| 2015/0372333 | A1* | 12/2015 | Odom ................. C07D 279/22 |
| | | | 429/108 |
| 2017/0062842 | A1* | 3/2017 | Huang ................. C07D 241/46 |
| 2017/0162916 | A1 | 6/2017 | Guarr et al. |
| 2019/0305381 | A1 | 10/2019 | Guarr et al. |

FOREIGN PATENT DOCUMENTS

| | | | |
|---|---|---|---|
| JP | H10134845 | A | 5/1998 |
| JP | H10144347 | A | 5/1998 |
| JP | 2001023687 | A * | 1/2001 |
| JP | 2004101729 | A | 4/2004 |
| JP | 2007522628 | A | 8/2007 |
| JP | 2009272170 | A | 11/2009 |
| JP | 2012214671 | A | 11/2012 |
| JP | 2013501337 | A | 1/2013 |
| JP | 2015-086201 | A | 5/2015 |
| JP | 2015086202 | A | 5/2015 |
| JP | 2015115110 | A | 6/2015 |
| JP | 2016033117 | A | 3/2016 |
| JP | 2016-103417 | A | 6/2016 |
| WO | 99/09111 | A1 | 2/1999 |
| WO | 2009102604 | A1 | 8/2009 |
| WO | 2009/141288 | A2 | 11/2009 |
| WO | 2016011393 | A1 | 1/2016 |
| WO | 2018098116 | A2 | 5/2018 |
| WO | 2019018741 | A1 | 1/2019 |

OTHER PUBLICATIONS

Examination Report No. 2 (AU Application No. 2018302335); dated May 28, 2020; 3 pages.
Notice of Acceptance (AU Application No. 2018302335); dated Jul. 3, 2020; 3 pages.
Odom, Susan et al.; "Synthesis and analysis of redox shuttles for overcharge protection in lithium-ion batteries", 1 page.
Odom, Susan et al.; "Increasing redox shuttle oxidation potentials to match high voltage cathodes in lithium-ion batteries", 1 page.
Narayana, Klishore et al.; "N-substituted phenothiazine derivatives as electrolyte additives for overcharge protection in lithium-ion batteries", 1 page.
Ergun, Selin et al.; "Overcharge performance of 3,7-disubstituted N-ethylphenothiazine derivatives in lithium-ion batteries", The Royal Society of Chemistry, 3 pages, Nov. 11, 2013.
Odom, Susan et al.; "A fast, inexpensive method for predicting overcharge performance in lithium-ion batteries", The Royal Society of Chemistry, 8 pages, Nov. 11, 2013.
Narayana, Kishore Anand et al.; "N-Substituted Phenothiazine Derivatives: How the Stability of the Neutral and Radical Cation Forms Affects Overcharge Performance in Lithium-Ion Batteries", 11 pages.
Casselman, Matthew et al.; "The fate of phenothiazine-based redox shuttles in lithium-ion batteries", 8 pages, Jan. 22, 2015.
Kaur, Aman Preet et al.; "Overcharge protection of lithium-ion batteries above 4 V with a perfluorinated phenothiazine derivative", 5 pages, Mar. 10, 2016.

International Search Report and Written Opinion ; Office Action (PCT Application No. PCT/US2015/040970); dated Jan. 5, 2016; 5 pages.
International Search Report and Written Opinion; Office Action (PCT Appication No. PCT/US17/62698); dated Feb. 2, 2018; 9 pages.
Notification of Reasons for Refusal; Office Action (JP Application No. 2017-502961); dated Jun. 24, 2019; 12 pages.
International Search Report and Written Opinion; Office Action (PCT Application No. PCT/US18/43048); dated Sep. 17, 2018; 16 pages.
International Search Report for Application No. PCT/US2015/040970 dated Jan. 5, 2016, 7 pages.
Adachi, Momoe et al., "Aromatic Compounds at Redox Shuttle Additives for 4 V Class Secondary Lithium Batteries" J. Electrochem. Soc. 1999, vol. 146(4)m pp. 1256-1261.
Buhrmester, Claudia et al., "Phenothiazine Molecules-Possible Redox Shuttle Additives for Chemical Overcharge and Overdischarge Protection for Lithium-Ion Batteries", J. Electrochem.Soc, 2006, vol. 153(2), pp. A288-A294.
Zhang, Lu et al., "Lithium Ion Batteries—New Developments", Chapter 7—Redox Shuttle Additives for Lithium-Ion Battery, Chapter 7, Feb. 2012, pp. 173-188.
International Application No. PCT/US2018/043048 filed Jul. 20, 2018, 66 pages.
International Search Report for Application No. PCT/US2017/062698 dated Feb. 2, 2018. 1 page.
International Search Report for Application No. PCT/US2018/043048 dated Sep. 17, 2018, 1 page.
Sevov, Christo S. et al., "Physical Organic Approach to Persistent, Cyclable, Low-Potential Electrolytes for Flow Battery Applications", J. A,/ Chem Soc., vol. 139, No. 8, 2017, pp. 2924-2927.
Zhang, Lu et al., "Molecular Engineering Towards Safer Lithium-Ion Batteries: a Highly Stable and Compatible Redox Shuttle for Overcharge Protection", Energy Environ. Sci., vol. 5, 2012, pp. 8204-8207.
Zhang, Lu et al., "Novel Redox Shuttle Additive for High-Voltage Cathode Materials", Energy Environ. Sci., vol. 4, 2011, pp. 2858-2862.
Non-Final Office Action (U.S. Appl. No. 16/269,009); dated Nov. 24, 2020; 23 pages.
English language abstract for JP2013501337 extracted from espacenet.com database on Jun. 17, 2021, 1 page.
English language abstract for JP2012214671 extracted from espacenet.com database on Jun. 17, 2021, 1 page.
English language abstract and machine-assisted English translation for JP2004101729 extracted from espacenet.com database on Jun. 17, 2021,15 pages.
English language abstract and machine-assisted English translation for JP2015115110 extracted from espacenet com database on Jun. 17, 2021, 32 pages.
English language abstract and machine-assisted English translation for JP2016033117 extracted from espacenet com database on Jun. 17, 2021, 23 pages.
English language abstract and machine-assisted English translation for JPH08195199 extracted from espacenet.com database on Jun. 17, 2021, 12 pages.

* cited by examiner

RECHARGEABLE ELECTROCHEMICAL CELL

RELATED APPLICATIONS

This application is the National Stage of International Patent Application No. PCT/US2017/062698, filed on Nov. 21, 2017, which claims priority to and all the advantages of U.S. Provisional Patent Application No. 62/425,226, filed on Nov. 22, 2016, the content of which is incorporated herein by reference.

FIELD OF THE DISCLOSURE

The present disclosure relates generally to rechargeable electrochemical cells. In certain embodiments, the present disclosure relates to a rechargeable lithium-ion cell including a particular redox shuttle. In other embodiments, the present disclosure relates to a redox flow battery including a particular redox active material.

BACKGROUND

Rechargeable electrochemical cells, particularly rechargeable lithium-ion cells, can exhibit excellent charge-discharge cycle life, little or no memory effect, and high specific and volumetric energy. However, lithium-ion cells typically exhibit an inability to tolerate recharging to potentials above the manufacturer's recommended end of charge potential without degradation in cycle life. Recharging to potentials above the manufacturer's recommended end of charge potential is typically described as overcharge. Overcharge generally occurs when a current is forced through the cells and the charge delivered exceeds the charge-storing capability of the cell. Overcharge of lithium-ion cells can lead to the chemical and electrochemical degradation of cell components, rapid temperature elevation, and can also trigger self-accelerating reactions in the cells.

To combat these problems, redox shuttles have been used. Redox shuttles are chemical compounds that are incorporated into lithium-ion cells for overcharge protection. Generally, the redox shuttle can be reversibly electrochemically oxidized at a potential slightly higher than the working potential of a positive electrode of the lithium-ion cell. Use of the redox shuttles allows lithium-ion cells to normally operate in a voltage range less than the redox potential of the redox shuttle. If the lithium-ion cells are charged to a level that exceeds their normal cell capacity (i.e., are "overcharged"), the voltage increases to the redox potential of the redox shuttle first and activates a redox mechanism, which proceeds as the only active component to transfer the excessive charge through the lithium-ion cells while minimizing damage. Use of such a mechanism inhibits overcharging.

Research and development has identified various options for redox shuttles. However, identifying shuttle candidates having both a suitably high redox potential and a sufficient service life has proven difficult. Many redox shuttles tend to chemically degrade over time or impede normal cell operation, thereby becoming useless. Accordingly, there remains an opportunity for improvement.

SUMMARY OF THE DISCLOSURE

The present disclosure provides a rechargeable battery comprising a positive electrode having a recharged potential, a negative electrode, a charge-carrying electrolyte, and an active material having the following structure:

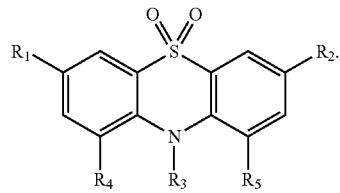

In this structure, $R_1$ and $R_2$ are independently an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. $R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group. $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

DETAILED DESCRIPTION

The present disclosure provides a device for storing electrical energy. In certain embodiments, the device may be a rechargeable lithium-ion cell (hereinafter described as a "cell"). The cell can alternatively be described as a battery, i.e., a rechargeable lithium-ion battery. The cell has a cell capacity, which is known in the art as an amount of electric charge the cell can deliver at a rated voltage. The capacity of the instant cell is not particularly limited and may be chosen by one of skill in the art. In other embodiments, the device may be a redox flow battery. In yet other embodiments, the device may be an electrochemical double layer capacitor, which may be described as a supercapacitor or ultracapacitor.

Rechargeable Lithium-Ion Cell

The cell may be sealed in a suitable case, e.g., in mating cylindrical metal shells such as in a coin-type cell, in an elongated cylindrical AAA, AA, C, or D cell casing, or in a replaceable battery pack. Alternatively, the cell may be sealed in a Li-ion format such as in an 18650 format, in a pouch cell, etc. The cell may be used in a variety of devices, including portable computers, tablet displays, personal digital assistants, mobile telephones, motorized devices (e.g., personal or household appliances and vehicles), instruments, illumination devices (e.g., flashlights), and heating devices. The cell may have particular utility in low-cost mass market electrical and electronic devices such as flashlights, radios, compact disc (CD) players, and the like, which heretofore have usually been powered by non-rechargeable batteries such as alkaline cells.

Positive Electrode:

The cell includes a positive electrode having a recharged potential. The cell may have a single positive electrode or more than one positive electrode. The terminology "positive electrode" may describe one or a pair of electrodes that, under typical circumstances and when the cell is fully charged, will have the highest potential the electrode(s) can achieve under normal operation. The terminology also typically describes the same physical electrode under all cell operating conditions even if the electrode temporarily (e.g., due to cell overdischarge) is driven to or exhibits a potential less than that of another (e.g., negative) electrode.

The positive electrode is not particularly limited and may be any known in the art. Non-limiting examples of the positive electrode may include $FeS_2$, $LiCoPO_4$, $LiFePO_4$, $Li_2FeS_2$, $Li_2FeSiO_4$, $LiMn_2O_4$, $LiMnPO_4$, $LiNiPO_4$, $LiV_3O_8$, $LiV_6O_{13}$, $LiVOPO_4$, $Li_3V_2(PO_4)_3$, $MnO_2$, $MoS_3$, sulfur, $TiS_2$, $TiS_3$, $V_2O_5$, $V_6O_{13}$, $LiCoO_2$, $LiNiMnCoO_2$, $LiNiCoAlO_2$, and/or combinations thereof. The positive electrode may include additives, e.g., carbon black, flake graphite, and the like. The positive electrode may be in any convenient form including foils, plates, rods, pastes, or as a composite made by forming a coating of the positive electrode material on a conductive current collector or other suitable support.

The terminology "recharged potential" typically describes a value $E_{cp}$ measured relative to $Li/Li^+$ by constructing a cell including the positive electrode, a negative electrode, a charge-carrying electrolyte, and no redox shuttle, carrying out a charge/discharge cycling test and observing the potential at which the positive electrode become delithiated during the first charge cycle to a lithium level corresponding to at least 90% of the available recharged cell capacity. For some positive electrodes (e.g., $LiFePO_4$), this lithium level may correspond to approximately complete delithiation (e.g., to $Li_0FePO_4$). For other positive electrodes (e.g., some electrodes having a layered lithium-including structure), this lithium level may correspond to partial delithiation.

Negative Electrode:

The cell includes a negative electrode. The cell may have a single negative electrode or more than one negative electrode. The terminology "negative electrode" may describe one of a pair of electrodes that, under normal circumstances and when the cell is fully charged, has the lowest potential. This terminology also typically describes the same physical electrode under all cell operating conditions even if such electrode is temporarily (e.g., due to cell overdischarge) driven to or exhibits a potential above that of the other (e.g., positive) electrode.

The negative electrode is not particularly limited and may be any known in the art. In various non-limiting embodiments, the negative electrode includes graphitic carbon, lithium metal, a lithium alloy, or combinations thereof. The negative electrode may include additives, e.g., carbon black. The negative electrode may be in any convenient form including foils, plates, rods, pastes, or as a composite made by forming a coating of the negative electrode material on a conductive current collector or other suitable support.

Charge-Carrying Electrolyte:

In addition to the above, the rechargeable lithium-ion cell also includes a charge-carrying electrolyte. The charge-carrying electrolyte includes a charge-carrying medium and a lithium salt. The charge-carrying electrolyte is not particularly limited and may be any known in the art. Typically, the charge-carrying electrolyte provides a charge-carrying pathway between the positive and negative electrodes, and initially includes at least the charge-carrying medium and the lithium salt. The charge-carrying electrolyte may include other additives typically utilized in the art. The charge-carrying electrolyte may be in any convenient form including liquids and gels.

The charge-carrying electrolyte may include an active material, such as the redox shuttle (as described in detail below) that may or may not be dissolved therein. For example, the charge-carrying electrolyte may be formulated without the redox shuttle and incorporated into a cell whose positive or negative electrode includes a dissolvable redox shuttle that can dissolve into the charge-carrying electrolyte after cell assembly or during the first charge-discharge cycle, so that the charge-carrying electrolyte includes a redox shuttle once the cell has been put into use.

Charge-Carrying Medium:

The charge-carrying electrolyte is not particularly limited and may be any known in the art. Non-limiting examples of suitable charge-carrying mediums include liquids and gels capable of solubilizing sufficient quantities of lithium salt and the redox shuttle so that a suitable quantity of charge can be transported from the positive electrode to the negative electrode. The charge-carrying medium can typically be used over a wide temperature range, e.g., from about −30° C. to about 70° C. without freezing or boiling, and is typically stable in the electrochemical window within which the electrodes operate. Non-limiting examples of charge-carrying mediums include, but are not limited to, ethylene carbonate, propylene carbonate, dimethyl carbonate, diethyl carbonate, ethylmethyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), and combinations thereof. In various embodiments, the charge-carrying medium includes ethylene carbonate, propylene carbonate, dimethyl carbonate, diethyl carbonate, ethylmethyl carbonate, and/or combinations thereof.

The charge-carrying medium is typically present in an amount of from 60% to 99% by weight, from 65% to 95% by weight, or from 70% to 90% by weight, each based on a total weight of the charge-carrying electrolyte. Alternatively, all values and ranges of values within those values described above are hereby expressly contemplated in various non-limiting embodiments.

Lithium Salt:

The lithium salt is also not particularly limited and may include any known in the art. Non-limiting examples of suitable lithium salts are stable and soluble in the chosen charge-carrying medium and perform well in the chosen lithium-ion cell, and can include or be $LiPF_6$, $LiBF_4$, $LiClO_4$, lithium bis(oxalato)borate ("LiBOB"), $LiN(CF_3SO_2)_2$, $LiN(C_2F_5SO_2)_2$, $LiAsF_6$, $LiC(CF_3SO_2)_3$ and/or combinations thereof.

The lithium salt is typically present in an amount of from 1 to 40, from 5 to 35, or from 10 to 30, parts by weight per 100 parts by weight of the charge-carrying electrolyte. Alternatively, all values and ranges of values within those values described above are hereby expressly contemplated in various non-limiting embodiments.

Redox Shuttle:

The cell includes a redox shuttle. In various embodiments, the terminology "redox shuttle" describes an electrochemically reversible moiety or compound that can become oxidized at the positive electrode, migrate to the negative electrode, become reduced at the negative electrode to reform the unoxidized (or less-oxidized) shuttle species, and migrate back to the positive electrode. Alternatively, the redox shuttle may be described as an electroactive compound, which may be heterocyclic, wherein the terminology "electroactive" is as understood by those of skill in the art. Alternatively, any one or more of the substituted phenothiazine 5,5-dioxides described below may be described as a redox shuttle and/or a compound that protects against overcharging.

A redox shuttle may have an oxidation potential above the recharged potential of the positive electrode and may serve as a cyclable redox shuttle providing cell overcharge protection. The terminology "oxidation potential" typically refers to a value $E_{1/2}$ which may be measured by dissolving the redox shuttle in the chosen charge-carrying electrolyte, measuring current versus applied voltage using cyclic voltammetry and a platinum or glassy carbon working electrode, a counter electrode and a suitable reference electrode that has been previously referenced to $Li/Li^+$ and determining the potentials $E_{pa}$ (i.e., the potential at which the peak anodic current is observed) and $E_{pc}$ (i.e., the potential at which the peak cathodic current is observed), relative to $Li/Li^+$. $E_{1/2}$ is typically taken as the average of $E_{pa}$ and $E_{pc}$. Shuttle oxidation potentials may be estimated (to provide a value "$E_{obs}$") by constructing a cell including the shuttle, carrying out a charge/discharge cycling test, and observing during a charging sequence the potential at which a voltage plateau indicative of shuttle oxidation and reduction occurs. The observed result may be corrected by the amount of the negative electrode potential vs. $Li/Li^+$ to provide an $E_{obs}$ value relative to $Li/Li^+$. Shuttle oxidation potentials may be approximated (to provide a value "$E_{calc}$") using modeling software such as GAUSSIAN 03 from Gaussian Inc. to predict oxidation potentials (e.g. for compounds whose $D_{1/2}$ is not known) by correlating model ionization potentials to the oxidation potentials and lithium-ion cell behavior of measured compounds.

The redox shuttle may, for example, have an oxidation potential from 3.5 to 5, from 3.6 to 5, from 3.7 to 5, from 3.8 to 5, from 3.9 to 4.9, from 4 to 4.8, from 4.1 to 4.7, from 4.2 to 4.6, from 4.3 to 4.5, or from 4.4 to 4.5 V as compared to $Li/Li^+$, above the recharged potential of the positive electrode. For example, one embodiment of a redox shuttle has an oxidation potential from 3.5 to 5 V as compared to $Li/Li^+$. In another embodiment, the redox shuttle has an oxidation potential from 4 to 5 V as compared to $Li/Li^+$. In still another embodiment, the redox shuttle has an oxidation potential from 3.5 to 4 V as compared to $Li/Li^+$. In a further embodiment, the redox shuttle has an oxidation potential from 3.7 to 3.9 V as compared to $Li/Li^+$, e.g. for $LiFePO_4$ cells. Alternatively, all values and ranges of values within those values described above are hereby expressly contemplated in various non-limiting embodiments.

The redox shuttle may be disposed in a charge-carrying electrolyte and/or in another location in the cell. When an attempt is made to charge the cell above this oxidation potential, the oxidized redox shuttle carries a charge quantity corresponding to the applied charging current to the negative electrode, which prevents or at least minimizes cell overcharge. In various embodiments, the redox shuttle is cyclable to provide at least 10, at least 30, at least 100, or at least 500 cycles of overcharge protection at a charging voltage sufficient to oxidize the redox shuttle and at an overcharge charge flow equivalent to 100% of the cell capacity during each cycle. In alternative embodiments, the aforementioned number of cycles is 500-1000, greater than 1,000, from 1,000 to 10,000, or even greater than 10,000. Alternatively, all values and ranges of values within those values described above are hereby expressly contemplated in various non-limiting embodiments. The redox shuttle is different from the positive electrode and typically has an oxidation potential different from and/or higher (e.g. more positive) than the recharged potential of the positive electrode. The potential of the redox shuttle may be slightly greater than the recharged potential of the positive electrode, less than the potential at which irreversible cell damage might occur, and less than the potential at which excessive cell heating or outgassing may occur.

In various embodiments, the substituted phenothiazine 5,5-dioxide is utilized alone as a redox shuttle or in combination with other redox shuttles. Alternative redox shuttles include substituted carbazoles, substituted phenothiazines, substituted 5,10-dihydrophenazines, and/or combinations thereof.

Substituted Phenothiazine-5,5-Dioxides

The substituted phenothiazine-5,5-dioxide typically has the following structure:

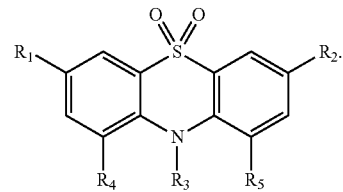

In various embodiments, $R_1$ and $R_2$ are independently an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. $R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group. $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. In embodiments where at least one of $R_4$ and $R_5$ is not a hydrogen atom, there is a shift in oxidation potential to more positive values, as well as improved stability as described in International Patent Application No. PCT/US2015/040970, filed on Jul. 17, 2015, the contents of which are incorporated herein by reference in their entirety.

In other embodiments, $R_1$ and $R_2$ are independently an alkyl group, a nitrile group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an oxo group, an alkyl ether group, a trialkylammoniumalkyl group, a phosphate group, a phosphonate group, or an alkyl phosphonate group. $R_3$ is an alkyl group having 1-6 carbon atoms or 1-12 carbon atoms or a haloalkyl group (e.g., mono-, di-, or tri-halo) having 1-12 carbon atoms. In one embodiment, both of $R_4$ and $R_5$ is hydrogen. In another embodiment, one of $R_4$ and $R_5$ is a hydrogen atom, whereas the other of $R_4$ and $R_5$ is not a hydrogen atom. In other embodiments, $R_3$ is an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-6 or 1-12 carbon atoms, or a trialkylammoniumalkyl group having 1-6 or 1-12 carbon atoms. Alternatively, all values and ranges of values within those values described above are hereby expressly contemplated in various non-limiting embodiments.

In further embodiments, $R_1$ and $R_2$ are independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, an alkyl ether group having 1-12 carbon atoms, or a trialkylammoniumalkyl group having 1 to 12 carbon atoms. In other embodiments, $R_4$ and $R_5$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, a haloacyl group, or a perhaloacyl group. Non-limiting examples of suitable alkyl groups are methyl, ethyl, propyl, iso-propyl, butyl, iso-butyl, sec-butyl, tert-butyl, neopentyl, n-pentyl, hexyl, octyl, and the like, as appreciated by those of skill in the art. Alternatively, all values and ranges of values within those values described above are hereby expressly contemplated in various non-limiting embodiments.

In still other embodiments, one of $R_4$ and $R_5$ is sterically bulky. In another embodiment, each of $R_4$ and $R_5$ is sterically bulky. The terminology "sterically bulky" is appreciated by those of skill in the art. For example, one or each of $R_4$ and $R_5$ may be $C_2$-$C_4$ alkyl group, such as an iso-propyl, butyl, iso-butyl, sec-butyl, tert-butyl group. These types of groups may shift a potential to a more positive value without sacrificing (or at least minimizing an effect on) stability of the compound. In some instances, these types of groups may actually enhance stability of the compound. Alternatively, one or each of $R_4$ and $R_5$ may be a $C_2$-$C_5$ alkyl group and may include those groups described above and neopentyl groups. In still other embodiments, each of $R_4$ and $R_5$ may be methyl and/or $CF_3$ groups.

In various embodiments, $R_1$ and $R_2$ are independently an alkyl group, a haloalkyl group (including perhaloalkyl), or an alkyl ether group and at least one of $R_3$, $R_4$, and $R_5$ is an alkyl group, a haloalkyl group (including perhaloalkyl), an alkyl ether group, an acyl group, or a haloacyl group. In other embodiments, each of $R_1$, $R_2$, $R_3$, $R_4$, and $R_5$ are chosen from alkyl groups, alkyl ether groups, acetyl groups, and $CF_3$ groups. Without intending to be bound by any particular theory, it is believed that substitution at some of these positions (such as, e.g., at $R_3$, $R_4$ and/or $R_5$) surprisingly increases the oxidation potential through a steric effect.

In one particular embodiment, $R_1$ and $R_2$ are independently an alkyl group or a nitrile group. $R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a tri alkyl ammoniumalkyl group, a phosphate group, a phosphonate group, an alkyl phosphonate group, or a trialkylanilinium group. $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

In still other embodiments, $R_3$ is chosen from —$CH_2CH_3$, —$CH_2CH_2OCH_2CH_2OCH_3$, —$CH_2CH_2OCH_3$, and -phenyl-$N(CH_3)^{3+}$. In other words, $R_3$ may be any one of these moieties. Moreover, it is contemplated that compounds having one of these $R_3$ moieties may have an oxidation potential of 4.26 to 4.40 V. Moreover, it is contemplated that such compound may have increased solubility in at least high lithium content carbonate electrolytes.

The redox shuttle, e.g. the substituted phenothiazine-5,5-dioxide, may be included in the cell in any amount as determined by one of skill in the art. In various embodiments, the substituted phenothiazine-5,5-dioxide is present in an amount of from 0.05 to 20, from 0.05 to 10, from 1 to 10, from 2 to 9, from 3 to 8, from 4 to 7, or from 5 to 6, parts by weight per 100 parts by weight of the charge-carrying electrolyte. Alternatively, all values and ranges of values within those values described above are hereby expressly contemplated in various non-limiting embodiments. Amounts of the substituted phenothiazine-5,5-dioxide may be chosen based on solubility, diffusion coefficients, the need for overcharge protection, etc.

Mixtures of two or more redox shuttles (including the phenothiazine-5,5-dioxide and one or more substituted phenothiazines, substituted carbazoles, substituted dihydrophenazines, or other redox shuttle) having different electrochemical potentials vs. Li/Li$^+$ may also be employed. For example, a first redox shuttle operative at 3.7 V and a second redox shuttle operative at 3.9 V may both be employed in a single cell. If after many charge/discharge cycles the first redox shuttle degrades and loses effectiveness, the second redox shuttle (which typically would not have been oxidized while the first redox shuttle was operative) can take over and provide a further (albeit higher $E_{1/2}$) margin of safety against overcharge damage. The redox shuttle can also provide overdischarge protection to a cell or to a battery of series-connected cells. Redox shuttles can also be used for cell balancing purposes as well as or even in lieu of overcharge protection. For example, redox shuttles could be used to reduce the cost of cell-balancing associated electronics.

The redox shuttle can be dissolved or is dissolvable in the charge-carrying electrolyte in an amount sufficient to provide overcharge protection at the intended charging rate. The maximum shuttle current for a singly ionized shuttle is typically given by the following equation, where F is Faraday's number, A is the electrode area, D is an effective diffusion constant of the redox shuttle species (taking into account both oxidized and reduced forms of the redox shuttle), C is the total concentration of the redox shuttle species, and d is the distance between the positive and negative electrodes:

$$I_{max}=FADC/d.$$

To obtain a large redox shuttle current, the charge-carrying electrolyte promotes a large diffusion constant D to the redox shuttle and/or supports a high redox shuttle concentration C. Accordingly, the charge-carrying electrolyte initially or eventually includes a dissolved quantity of the substituted phenothiazine 5,5-dioxide and/or other redox shuttles. The redox shuttle diffusion constant D typically increases as the viscosity of the charge-carrying electrolyte decreases. Non-limiting concentrations of the substituted phenothiazine 5,5-dioxide and/or other redox shuttle in the charge-carrying electrolyte are about 0.02 M up to a limit of solubility, about 0.05 M up to a limit of solubility, more than 0.1 M up to a limit of solubility, about 0.2 M up to a limit of solubility or about 0.3 M up to a limit of solubility. The concentration of the substituted phenothiazine 5,5-dioxide and/or other redox shuttle may be increased by incorporating a suitable co-solvent in the charge-carrying electrolyte. Non-limiting co-solvents include acetonitrile, benzene, ethers, esters, lactones, pyridine, tetrahydrofuran, toluene, and/or combinations thereof. In other embodiments, the co-solvent is chosen from ethylene carbonate, propylene carbonate, dimethyl carbonate, diethyl carbonate, ethylmethyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), and combinations thereof. In still other embodiments, the co-solvent is chosen from ethylene carbonate, propylene carbonate, dimethyl carbonate, diethyl carbonate, ethylmethyl carbonate, and/or combinations thereof.

In various embodiments, the redox-shuttle may be 3,7-bis(tert-butyl)-10-methylphenothiazine-5,5-dioxide; 3,7-bis (tert-butyl)-10-(p-tolyl)-phenothiazine-5,5-dioxide; 3,7-bis (tert-butyl)-10-(9-trifluoromethylphenyl)-phenothiazine-5, 5-dioxide; or other phenothiazine-5,5-dioxides analogous to the aforementioned compounds; and/or any analogs having substitution at any position such as $C_1$-$C_{20}$ alkyl, alkyl ether or oligoether, trialkylammoniumalkyl, or other solubilizing groups. In other embodiments, the solubilizing group may be any known in the art. For example, the solubilizing groups may be as described in U.S. Pat. No. 6,445,486, which is expressly incorporated herein by reference in various non-limiting embodiments. Moreover, it is also contemplated that any compounds described in the Examples below may be utilized in any embodiments described herein in various non-limiting embodiments.

Referring back to the cell itself, the cell may also include a porous cell separator disposed between the positive and negative electrodes and through which charge-carrying species (including the oxidized or reduced substituted phenothiazine-5,5-dioxide) may pass.

In various embodiments, the redox shuttle provides overcharge protection to the cell after at least 30, 40, 50, 60, 70, 80, 90, 100, 200, 300, 400, 500, 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, or even greater, charge-discharge cycles at a charging voltage sufficient to oxidize the redox shuttle and at an overcharge charge flow equivalent to 100% of the cell capacity during each charge-discharge cycle. Alternatively, all values and ranges of values within those values described above are hereby expressly contemplated in various non-limiting embodiments.

This disclosure also provides an article including the cell and an array of cells. The article may be any known in the art that utilizes cells (or batteries), e.g. hand-held devices, flashlights, power tools, or any of those described above. The array of cells may also be any known in the art.

Redox Flow Battery

In an embodiment, the redox shuttle may also be used as an active catholyte material in redox flow batteries. Redox flow batteries include an electrochemical cell containing at least two electrodes and at least two electroactive materials. At least one of the electroactive materials is in the form of an electrolyte solution or slurry, including the electroactive material, a suitable solvent, and optionally an added electrolyte salt for improved ionic conductivity. The electrolyte solution may be moved from a separate tank through a cell using a pump, gravity, pressure, or other suitable means. The electrochemical cell may be divided into an anode and a cathode chamber by an ion exchange or microporous membrane that serves to minimize mixing of the different electroactive materials (often described as "crossover"). In an alternative embodiment, the electrochemical cell may be a membrane-free system that can maintain separation of the active species by laminar flow. Transport of the electrolyte salt anion and/or cation across the membrane can occur, which facilitates an electrochemical reaction between the electroactive materials (provided that the electrodes are connected by an external electrical circuit). In an embodiment, multiple electrochemical cells can be connected in series or in parallel to form a cell stack for producing a desired level of current and/or voltage.

Redox flow batteries typically utilize solution phase materials in both the anode and cathode compartments (which are often described as "anolyte" and "catholyte", respectively). Alternatively, redox flow batteries may utilize an intercalation-type electrode, such as graphite or the like, as the anode or cathode.

Since the electroactive materials for the redox flow battery are typically stored in a tank or other suitable container outside of the electrochemical cell, power and energy are effectively decoupled and energy storage can be readily and inexpensively scaled. While the energy density of the redox flow battery is generally too low for mobile applications, the potential low cost and scalability renders the redox flow battery as being well suited for grid or energy storage applications.

Embodiments of the redox shuttle described in detail above may be used as a redox active or catholyte material for a redox flow battery, at least in part because the redox shuttle has one or more of a low manufacturing cost, a high solubility, a rapid electrochemical response, a high oxidation potential, and excellent durability. In an embodiment, the catholyte material is present in an amount of from about 2 to 80 parts by weight per 100 parts by weight of the charge-carrying electrolyte. In an example, 3,7-bis(tert-butyl)-10-methylphenothiazine-5,5-dioxide may be used as a catholyte material, may be readily prepared from inexpensive materials, is soluble in propylene carbonate to over 1.4 M, exhibits a desirable electrochemical oxidation at 4.28V as compared to $Li/Li^+$, and is stable in both the neutral and oxidized form.

Electrochemical Double Layer Capacitor

In another embodiment, the redox shuttle may be used as an active catholyte material in electrochemical double layer (EDL) capacitors, which are often also described as supercapacitors or ultracapacitors. EDL capacitors differ from batteries in that the electrical energy is stored by the physical process of building charge on the surface of inert electrodes rather than storing energy in an electrochemical reaction (as in batteries). The electrical current that serves to build charge on the surface of an electrode may be described as capacitive or nonfaradaic current. Current that serves to carry out a chemical reaction may be described as faradaic current or, with electrochemical reactions within an EDL capacitor, pseudocapacitance.

Hybrid supercapacitors are devices that combine the properties of batteries and EDL capacitors, and can store electrical energy in both faradaic and nonfaradaic processes. A common type of hybrid supercapacitor is an EDL capacitor with the charge storage capability enhanced by incorporating a redox active material in the electrolyte. Embodiments of the redox shuttle described in detail above may also be used as the redox active material for EDL capacitors, particularly hybrid supercapacitors, at least in part because the redox shuttle has one or more of a low manufacturing cost, a high solubility, a rapid electrochemical response, a high oxidation potential, and excellent durability.

Additional Embodiments

In one additional embodiment, this disclosure provides a redox shuttle for a lithium-ion cell having the following structure:

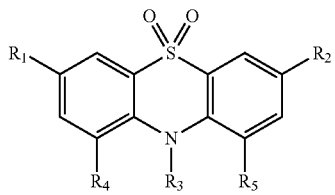

wherein:

$R_1$ and $R_2$ are independently an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group;

$R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group; and $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

In a further embodiment, this disclosure provides a catholyte material for a redox flow battery having the following structure:

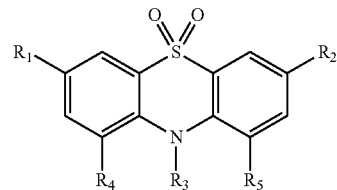

wherein:

$R_1$ and $R_2$ are independently an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group;

$R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group; and $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

In still a further embodiment, this disclosure provides a phenothiazine-5,5-dioxide having the following structure:

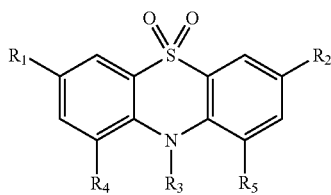

wherein:

$R_1$ and $R_2$ are independently an alkyl group or a nitrile group;

$R_3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group; and $R_4$ and $R_5$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

EXAMPLES

Various substituted phenothiazine-5,5-dioxides are synthesized and evaluated to determine oxidation potential. Additional theoretical calculations of oxidation potential are also performed on compounds not actually synthesized. The calculation of oxidation potential is based on the work of R. L. Wang et al., as set forth in Wang, R. L.; Buhrmester, C.; Dahn, J. R. J. Electrochem. Soc. 2006, 153, A445-A449, which is expressly incorporated by reference herein in various non-limiting embodiments.

The oxidation potential $E^0$ of a redox shuttle candidate relative to a lithium-ion cell can be determined by comparing the difference in standard free energies between the B3LYP energy $G^0$ (in electronvolts) between the shuttle S and its radical cation $S^+$:

$$E^0(S) = -\frac{[G^0(S) - G^0(S^+)]}{e} - 1.46 \text{ V}$$

All electrochemical measurements are performed in propylene carbonate including 0.2M tetraethylammonium tetrafluoroborate as a supporting electrolyte. Oxidation potentials were determined by averaging the anodic and cathodic peak potentials obtained via cyclic voltammetry (100 mV/s) or from differential pulse voltammetry. Ferrocene was used as an internal standard having $E_{OX}$=3.25 V vs. Li/Li$^+$.

The calculations, both theoretical and actual, of various substituted phenothiazines-5,5-dioxides are set forth in the table below.

| $R_1$ and $R_2$ | $R_3$ | $R_4$ and $R_5$ | E calc (Li/Li$^+$) | E exp (Li/Li$^+$) |
|---|---|---|---|---|
| t-Bu | CH$_3$ | H | 4.27 | 4.28 |
| t-Bu | BrCH$_2$CH$_2$CH$_2$ | H | 4.19 | 4.31 |
| t-Bu | 4-CH$_3$-phenyl | H | 4.07 | 4.30 |
| t-Bu | 4-CF$_3$-phenyl | H | 4.14 | 4.36 |
| t-Bu | 4-NO$_2$-phenyl | H | N/A | 4.39 |
| CF$_3$ | CH$_3$ | H | 4.72 | N/A |

The phenothiazine-5,5-dioxides are generally prepared by preparing a phenothiazine including the $R_1$ and $R_2$ groups and optionally including the $R_4$ and $R_5$ groups, then attaching the $R_3$ group, and then oxidizing to form a dioxide. Typically, the $R_4$ and $R_5$ groups are attached early, e.g. when forming the ring. Alternatively, the $R_4$ and $R_5$ groups may be attached late, e.g. after attaching the $R_3$ group and before oxidation. Specific examples of precursors for forming phenothiazine-5,5-dioxides, as well as specific examples of phenothiazine-5,5-dioxides are described below.

Synthesis of 3,7-bis-tert-butylphenothiazine

The precursor 3,7-bis-tert-butylphenothiazine is prepared according to the following synthesis. About 10 g (50.25 mmol, 1 eq) of phenothiazine and about 9 g (67.5 mmol, 1.3 eq) of aluminum chloride are placed in a round bottom flask. About 120 mL of dichloromethane is added and the reacted mixture (or reaction) is placed in a water/ice bath. About 27.3 mL (251.16 mmol, 5 eq) of tert-butyl chloride are added dropwise. After the addition is complete, the reacted mixture is left stirring at 0-5° C. for about 30 minutes, and the reacted mixture is then quenched with about 27 g (329.15 mmol, 6.6 eq) of sodium acetate dissolved in about 1 L of water. This mixture is then stirred vigorously until a color change from dark pink to green occurs. Then, the organic layer is separated and about 200 mL of heptane is added. The volume is reduced by rotary evaporation until the solid crashes out, is stirred vigorously overnight, and is filtered by gravity filtration to produce about 15.54 g (99.5% yield) of 3,7-bis-tert-butylphenothiazine.

In an example, the precursor 3,7-bis-tert-butylphenothiazine may be used to prepare the following 10-substituted 3,7-bis-tert-butylphenothiazines: 3,7-bis(tert-butyl)-10-methylphenothiazine; 3,7-bis(tert-butyl)-10-(p-tolyl)phenothiazine; 3,7-bis(tert-butyl)-10-(p-trifluoromethylphenyl) phenothiazine; 3,7-bis(tert-butyl)-10-(p-nitrophenyl) phenothiazine; and 3,7-bis(tert-butyl)-10-(3-bromopropyl) phenothiazine.

Additional Precursors:

The synthesis of other precursors that may be used to form phenothiazine-5,5-dioxides are set forth below.

Synthesis of 3,7-bis(tert-butyl)-10-methylphenothiazine 3,7-bis(tert-butyl)-10-methylphenothiazine is prepared according to the following synthesis. About 10 g (32.15 mmol, 1 eq) of 3,7-bis-tert-butylphenothiazine, about 1.96 g (11.25 mmol, 0.35 eq) of sodium dithionite, about 6.33 g (59.77 mmol, 1.9 eq) of sodium carbonate, and about 2.88 g (12.21 mmol, 0.38 eq) of methyltributylammonium chloride are added to a round bottom flask. About 200 mL of acetonitrile and about 4.4 mL (70.7 mmol, 2.2 eq) are added. The reacted mixture (i.e., the reaction) is heated to reflux and left overnight. Then, the reaction is cooled to room temperature and about 200 mL of water is added, which crashes out the product. The reaction is filtered by gravity filtration, to produce about 9.21 g (88% yield) of 3,7-bis(tert-butyl)-10-methylphenothiazine.

Synthesis of 3,7-bis(tert-butyl)-10-(p-tolyl)phenothiazine 3,7-bis(tert-butyl)-10-(p-tolyl)phenothiazine is prepared according to the following synthesis. 4-iodobenzene (0.79 g, 3.62 mmol, 1.2 eq) is melted in a round bottom flask. About 1.3 g (9.4 mmol, 3 eq) of potassium carbonate and about 1 g (3.21 mmol, 1 eq) of 3,7-bis-tert-butylphenothiazine, and some copper powder is added. After about 6 hours at reflux, the reacted mixture is cooled and dried via rotary evaporation. The remainder is dissolved in ethanol and filtered. The solution is left to crystallize overnight, and excess ethanol is filtered off from the crystals. The synthesis produced about 0.61 g (48% yield) of 3,7-bis(tert-butyl)-10-(p-tolyl)phenothiazine.

Synthesis of 3,7-bis(tert-butyl)-10-(p-trifluoromethylphenyl)phenothiazine 3,7-bis(tert-butyl)-10-(p-trifluoromethylphenyl)phenothiazine is prepared according to the following synthesis. 3,7-bis-t-butyl phenothiazine (5 g, 0.016 mol) is dissolved under stirring in about 50 mL N-methylpyrrolidinone (NMP) in a glove box under a nitrogen atmosphere. NaH as a 60% wt. suspension in mineral oil (1.0 g, 0.024 mol, 1.5 eq) is added at once, and the reaction mixture is stirred for about 60 minutes to form an orange suspension. 1-fluoro-4-trifluoromethylbenzene (5 mL, 0.040 mol, 2.5 eq) is added to the reaction mixture dropwise, and the flask is then transferred in the hood into an oil bath and pre-heated at about 80° C. The reaction is continued at the foregoing temperature for about 5 hours until a small sample analyzed by thin layer chromatography (eluent: hexane/ethylacetate: 8/2) indicates the completion of the reaction. The flask is then transferred into a water-ice bath, cooled to 0-5° C. and diluted with about 100 mL deionized water under vigorous stirring. The orange emulsion formed is extracted with about 3×100 mL dichloromethane, and the combined organic phase is washed with about 3×100 mL water and about 1×50 mL brine. After drying the dichloromethane solution over $MgSO_4$, (5 g), the solvent is evaporated under reduced pressure and the orange crystals are washed with about 25 mL cold methanol and about 25 mL cold hexane. After traces of solvents are removed by drying the product in a vacuum oven at room temperature for 12 hours, 6.3 g (yield: 86.3%) of pale yellow crystals (3,7-bis(tert-butyl)-10-(p-trifluoromethylphenyl)phenothiazine) are obtained.

Synthesis of 3,7-bis(tert-butyl)-N-nitrophenylphenothiazine 3,7-bis(tert-butyl)-N-nitrophenylphenothiazine is prepared according to the following synthesis. 3,7-bis-tert-butylphenothiazine (2 g, 6.43 mmol, 1 eq) is dissolved in about 30 mL of dry tetrahydrofuran and about 0.77 g NaH, 60% dispersion in mineral oil (19.25 mmol, 3 eq). About 2.82 g of p-nitrofluorobenzene (19.98 mmol, 3 eq) is added. The reaction mixture is put under $N_2$, stirred overnight, and then washed with water and the tetrahydrofuran is removed via rotary evaporation. The synthesis produced about 2.55 g (92% yield) of 3,7-bis(tert-butyl)-N-nitrophenylphenothiazine.

Synthesis of 3,7-bis(tert-butyl)-10-(3-bromopropyl) phenothiazine 3,7-bis(tert-butyl)-10-(3-bromopropyl)phenothiazine is produced according to the following synthesis. A 100 ml flask is charged with about 4.7 g of phenothiazine, about 0.78 g of sodium dithionite, about 2.6 g of sodium carbonate, about 0.52 g of methyltributylammonium chloride, and about 30 mL of acetonitrile. The combination is allowed to stir, and about 17 mL of 1,3-dibromopropane is added. The reaction mixture is heated to reflux and allowed to stir for about 44 hours. The reaction mixture is then quenched with water, and the desired product is extracted with about 600 mL of dichloromethane (100 mL washes). The organic washes are dried over MgSO$_4$, and the dichloromethane is removed by rotary evaporation, resulting in an amber-brown colored liquid.

The reaction mixture is further purified by adding the reaction mixture to about 50 mL of acetonitrile and about 50 mL of hexane in a separatory funnel. The hexane layer is washed with about 3×50 mL of acetonitrile, and the hexane is removed by rotary evaporation to give a slightly tan clear oil. The oil is dried in a vacuum oven to yield about 2.14 g of substantially pure 3,7-bis(tert-butyl)-10-(3-bromopropyl) phenothiazine.

General Synthesis of 3,7-bis-tert-butylphenothiazine-5,5-dioxides

The 3,7-bis-tert-butylphenothiazine-5,5-dioxides are generally prepared according to the following synthesis. One equivalent of 3,7-bis(tert-butyl)-10-substituted phenothiazine is dissolved in 2:1 dichloromethane:acetic acid, and about 2.5 equivalents of H$_2$O$_2$ is added. The reaction mixture is heated to reflux overnight, then quenched with water, dried over MgSO$_4$, and further dried via rotary evaporation. The reaction mixture is then triturated in water. The synthesis typically produced approximately 50% of the desired 3,7-bis-tert-butyl-10-substituted phenothiazine-5,5-dioxide.

The specific syntheses of several of the foregoing phenothiazine-5,5-dioxides are set forth below.

Synthesis of 3,7-bis(tert-butyl)-10-(3-bromopropyl) phenothiazine-5,5-dioxide Synthesis of 3,7-bis(tert-butyl)-10-(3-bromopropyl)phenothiazine-5,5-dioxide is prepared according to the following synthesis. A 250 ml flask is charged with about 2.2 g of 3,7-bis(tert-butyl)-10-(3-bromopropyl)phenothiazine and about 90 mL of dichloromethane. To this mixture, about 13 mL of acetic acid and about 8 mL of 30% H$_2$O$_2$ is added. The reaction mixture is brought to reflux for about 4 hours, and the reaction mixture is quenched with water. The product is extracted with about 3×50 mL of dichloromethane and dried over MgSO$_4$. The MgSO$_4$ is filtered off and the solvent is removed by rotary evaporation to give a thick white solid. The solid is dried in a vacuum oven for at least three hours to produce (yield) about 1.9 g, approximately 80%, of 3,7-bis(tert-butyl)-10-(3-bromopropyl)phenothiazine-5,5-dioxide.

Synthesis of 3,7-bis-t-butyl-10-(p-trifluoromethylphenyl)phenothiazine-5,5-dioxide 3,7-bis-t-butyl-10-(p-trifluoromethylphenyl)phenothiazine-5,5-dioxide is prepared according to the following synthesis. 3,7-bis-t-butyl-10-(p-trifluoromethylphenyl)phenothiazine (2.5 g, 5.4 mmol) is added to a mixture of acetic acid (12.5 mL) and acetic anhydride (25 mL) to form a pink suspension. The pink suspension is vigorously stirred at room temperature for about 5 minutes. A 30% aqueous solution of H$_2$O$_2$ (2.7 g, 32.92 mmol, 6 eq) is added at once, and the flask is transferred into an oil bath pre-heated at 65° C. Within about 5 minutes, a violet solution is formed and after another 5 minutes, the color of the solution turns to a pale yellow. During the next 30 minutes, a white solid separates and the flask is transferred to a water bath and cooled to room temperature. The white crystals are filtered, washed with about 3×50 mL deionized water, and dried at room temperature under reduced pressure. The amount of white crystals recovered is about 1.4 g. The filtrate is added dropwise, using a dropping funnel, into 500 mL deionized water when a milk-like suspension is obtained. The suspension is neutralized to pH=7 using a concentrated NaOH solution when a tan solid separates. The slurry is filtrated, washed with water, and then dried. The synthesis produced (yield) about 1 g, 89.69%, of 3,7-bis-t-butyl-10-(p-trifluoromethylphenyl)phenothiazine-5,5-dioxide.

It is to be appreciated that the examples set forth above utilize 3,7-bis-t-butyl substituents for each of syntheses, but other 3,7-substituents are also possible.

Additional Embodiments

Additional compounds are also synthesized, as set forth below. More specifically, the synthesis of three intermediates is described followed by the synthesis of various embodiments of phenothiazine-5,5-dioxides. These compounds, as set forth in the table below, are evaluated in the same way as is described above.

| $R_1$ and $R_2$ | $R_3$ | $R_4$ and $R_5$ | E calc (Li/Li$^+$) | E exp (Li/Li$^+$) |
|---|---|---|---|---|
| t-Bu | —CH$_2$CH$_3$ | H | N/A | 4.26 |
| t-Bu | —CH$_2$CH$_2$OCH$_2$CH$_2$OCH$_3$ | H | 4.09 | 4.27 |
| t-Bu | —CH$_2$CH$_2$OCH$_3$ | H | N/A | 4.31 |

Intermediate

3,7-Di(tert-butyl)-10-(N-2-(2-methoxyethoxy)ethyl) phenothiazine 3,7-Di-t-butyl phenothiazine (5 g, 16.05 mmol) was dissolved under stirring in 50 mL NMP, in a 250-mL round bottomed, 2-necked flask fitted with septa, in the glove box. NaH as a 60% wt. suspension in mineral oil (1.3 g, 32.1 mmol, 2 eq) was added at once and the reaction mixture was stirred for 30 minutes. 2-Methoxyethoxyethyl tosylate (5.5 g, 20.06 mmol, 1.25 eq) was dissolved in 10 mL NMP and added to the reaction mixture and the stirring was continued for 10 more minutes. The flask was then transferred into an oil bath pre-heated at 60° C., in the hood. To the flask, a nitrogen flow was added via a syringe needle through one septum, with a short needle inserted as well, as a bleed point in another septum. The mixture was stirred for 5 hours at 60° C., and then allowed to cool to room temperature. The flask was next transferred into a water-ice bath, and the reaction mixture was cooled to 0-5° C. and diluted with 200 mL deionized water under vigorous stirring. The yellow emulsion that formed was extracted with 3×100 mL hexanes and combined hexanes solution was washed with 3×150 mL water and 1×150 mL brine. After drying the hexanes solution on MgSO$_4$, the solvent was evaporated under reduced pressure to give 16.69 g of crude product, as yellow oil. The crude material was purified by column chromatography using as eluent a mixture of hexanes and ethyl acetate (80/20, v/v). The amount of product recovered after column: 15 g of colorless viscous oil (yield: 100%).

Embodiment of Phenothiazine-5,5-Dioxide: 3,7-Di(tert-butyl)-10-(N-2-(2-methoxyethoxy)ethyl)phenothiazine-5,5-dioxide 3,7-Di(tert-butyl)-10-(N-2-(2-methoxyethoxy)ethyl)phenothiazine (6 g, 14.5 mmol) was added to a mixture of acetic acid (30 mL) and acetic anhydride (60 mL) and the pink suspension formed was vigorously stirred at room temperature for 5-10 minutes. Hydrogen peroxide as 30 wt. % aqueous solution (6 eq) was added at once and the flask was transferred into an oil bath pre-heated at 70° C. Within 30 minutes a yellow solution was formed and the flask was immediately transferred to an ice-water bath and cooled to room temperature. The reaction mixture was added dropwise, using a dropping funnel, into 500 mL deionized water and the emulsion formed was extracted with 3×100 mL ethyl acetate. The combined ethyl acetate solution was washed with 2×150 mL water, 2×100 mL 10 wt. % $Na_2CO_3$, and finally 2×150 mL water, dried over 5 g of $MgSO_4$ and the solvent was removed by rotary evaporation at reduced pressure to afford 5.1 g of pale yellow crude product. After purification by column chromatography (eluent: a mixture of hexanes and ethyl acetate 80/20, v/v) a white crystalline product was produced (3 g, yield: 46%). Melting Point (M.p.)=84.5° C., by differential scanning calorimetry (DSC).

Intermediate 3,7-Di(tert-butyl)-10-(N-2-methoxyethyl)phenothiazine 3,7-Di-t-butyl phenothiazine (10 g, 32.1 mmol) was dissolved under stirring in 100 mL NMP, in a 500-mL round bottomed, 3-necked flask fitted with septa, in the glove box. NaH as a 60% wt. suspension in mineral oil (2 g, 48.2 mmol, 1.5 eq) was added at once and the reaction mixture was stirred for 60 minutes. 2-Bromoethyl methyl ether (6.7 g, 48.2 mmol, 1.5 eq) was dissolved in 10 mL NMP and added to the reaction mixture dropwise and the stirring was continued for 10 more minutes. The flask was then transferred into an oil bath pre-heated at 60° C., in the hood. To the flask, a nitrogen flow was added via a syringe needle through one septum, with a short needle inserted as well, as a bleed point in another septum. The mixture was stirred for 1 hour at 60° C., and then allowed to cool to room temperature and stirred overnight. The crude reaction mixture was then quenched in 500 mL deionized water, under vigorous stirring. The milky emulsion that formed was extracted with 3×150 mL hexanes and combined hexanes solution was washed with 4×150 mL water and 1×150 mL brine. After drying the hexanes solution on 10 g of $MgSO_4$, the solvent was evaporated under reduced pressure to give 11.81 g of crude product, as yellow oil. After trituration with about 10 mL of iso-propanol and drying, 11.5 g (yield: 97%) of pure product, as colorless oil was produced.

Embodiment of Phenothiazine-5,5-Dioxide: 3,7-Di(tert-butyl)-10-(N-2-methoxyethyl)phenothiazine-5,5-dioxide 3,7-Di(tert-butyl)-10-(N-2-methoxyethyl)phenothiazine (5.5 g, 14.5 mmol) was added to a mixture of acetic acid (30 mL) and acetic anhydride (60 mL) and the pink suspension formed was vigorously stirred at room temperature for 5-10 minutes. Hydrogen peroxide as 30 wt. % aqueous solution (6 eq) was added at once and the reaction mixture started to warm up gradually to 60° C. within 30 minutes when a brown solution was formed and the flask was transferred into an ice-water bath and cooled to room temperature. The reaction mixture was added dropwise, using a dropping funnel, into 500 mL deionized (DI) water and the emulsion formed was extracted with 3×100 mL ethyl acetate. The combined ethyl acetate solution was washed with 2×150 mL water, 2×100 mL 10 wt. % $Na_2CO_3$, and finally 2×150 mL water, dried over 5 g of $MgSO_4$ and the solvent was removed by rotary evaporation at reduced pressure to afford 5.1 g of pale yellow solid product. After purification by column chromatography (eluent: a mixture of hexanes and ethyl acetate 80/20, v/v) a white crystalline product was produced (2.8 g, yield: 46.8%). M.p.=51.7° C., by DSC.

Intermediate 3,7-di(tert-butyl)-10-(N-ethyl)phenothiazine 3,7-Di-t-butyl phenothiazine (14 g, 45 mmol) was dissolved under stirring in 100 mL NMP, in a 250-mL round bottomed, 2-necked flask fitted with septa, in the glove box. NaH as a 60% wt. suspension in mineral oil (2.7 g, 67.5 mmol, 1.5 eq) was added at once and the reaction mixture was stirred for 60 minutes at room temperature. Ethyl iodide (14 g, 90 mmol, 2 eq) was dissolved in 10 mL NMP and added to the reaction mixture dropwise. The reaction mixture was stirred for about 5 hours at room temperature, and then quenched with 500 mL deionized water under vigorous stirring. The pale yellow emulsion formed was extracted with 3×200 mL hexanes and combined hexanes solution was washed with 3×150 mL water and 1×150 mL brine. After drying the hexanes solution on $MgSO_4$, the solvent was evaporated under reduced pressure to give 16.5 g of crude product. After recrystallization from iso-propanol, filtration and removal of the traces of solvent under reduced pressure, 15 g (yield: 98.3%) of pure product was produced. M.p.=92.91° C., by DSC.

Embodiment of Phenothiazine-5,5-Dioxide: 3,7-di(tert-butyl)-10-(N-ethyl)phenothiazine-5,5-dioxide 3,7-Di(tert-butyl)-10-(N-ethyl)phenothiazine (10 g, 29.45 mmol) was added to a mixture of acetic acid (75 mL) and acetic anhydride (100 mL) and the pink suspension formed was vigorously stirred at room temperature for 5-10 minutes. Hydrogen peroxide as 30 wt. % aqueous solution (6 eq) was added at once and the reaction mixture started to warm up gradually to 60° C. within 2 hours, when a brown solution was formed and the flask was transferred to an ice-water bath and cooled to room temperature. The crude reaction mixture was quenched in 1 L of DI water and the slightly orange precipitate was filtered and thoroughly washed with 2×250 mL DI water, 1×150 mL 10 wt. % $Na_2CO_3$, and finally 2×250 mL water until neutral pH. The solid was dried in vacuum oven at room temperature for 48 hours, to afford 10.6 g of crude product which was purified by trituration with 25 mL hexane and two successive recrystallizations from methanol. White crystals: 9.2 g, yield 85%. M.p.=176° C., by DSC.

It is to be understood that the appended claims are not limited to express and particular compounds, compositions, or methods described in the detailed description, which may vary between particular embodiments that fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and/or in combination and provides adequate support for specific embodiments within the scope of the appended claims.

It is also to be understood that any ranges and subranges relied upon in describing various embodiments of the present disclosure independently and collectively fall within the scope of the appended claims and are understood to describe and contemplate all ranges, including whole and/or fractional values therein, even if such values are not expressly written herein. One of skill in the art readily recognizes that the enumerated ranges and subranges sufficiently describe and enable various embodiments of the present disclosure and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims and may be relied upon individually and/or collectively and provide adequate support for specific embodiments within the scope of the appended claims.

In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The disclosure has been described in an illustrative manner and it is to be understood that the terminology which has been used is intended to be in the nature of words of description rather than of limitation. Many modifications and variations of the present disclosure are possible in light of the above teachings and the disclosure may be practiced otherwise than as specifically described.

What is claimed is:

1. A rechargeable electrochemical cell comprising:
    a positive electrode having a recharged potential;
    a negative electrode;
    a charge-carrying electrolyte; and
    an active material having the following structure:

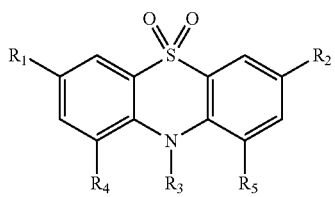

wherein:
    $R_1$ and $R_2$ are independently a nitrile group, an acyl group, an acyloxy group, an acetyl group, a haloacetyl group, an alkoxy group, an acetamido group, an amido group, an aryl group, an aralkyl group, an aryl carboxyl group, a benzoyl group, a carbamoyl group, a carboxy group, a cyano group, a formyl group, a halo group, a haloacetamido group, a haloacyl group, a haloaryl group, an arylhaloalkyl group, a methylsulfonyloxyl group, a nitro group, phosphate group, or a phosphonate group;
    $R_3$ is, an alkylaryl group, a trialkylammoniumalkyl group, a phosphate group, a phosphonate group, an alkyl phosphonate group, or a trialkylanilinium group; and
    $R_4$ and $R_5$ are independently hydrogen, an alkyl group, a haloalkyl group, a perhaloalkyl group, an acyl group, an acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

2. The rechargeable electrochemical cell as set forth in claim 1 wherein $R_1$ and $R_2$ are independently a nitrile group, an acyl group, an acyloxy group, an acetyl group, a haloacetyl group, an alkoxy group, an acetamido group, an amido group, an aryl group, an aralkyl group, an aryl carboxyl group, a benzoyl group, a carbamoyl group, a carboxy group, a cyano group, a formyl group, a halo group, a haloacetamido group, a haloacyl group, a haloaryl group, a methylsulfonyloxyl group, a nitro group, a phosphate group, or a phosphonate group.

3. The rechargeable electrochemical cell as set forth in claim 1 wherein $R_1$ and $R_2$ are independently a trifluoromethyl group, a cyano group or an alkoxy group.

4. The rechargeable electrochemical cell as set forth in claim 1 wherein $R_3$ is a trialkylammoniumalkyl group having 1-12 carbon atoms.

5. The rechargeable electrochemical cell as set forth in claim 1 wherein $R_4$ and $R_5$ are independently an alkyl group having 1-12 carbon atoms, a haloalkyl group having 1-12 carbon atoms, a perhaloalkyl group having 1-12 carbon atoms, an acyl group, a haloacyl group, or a perhaloacyl group.

6. The rechargeable electrochemical cell as set forth in claim 1 wherein $R_4$ and $R_5$ are independently a $C_2$-$C_4$ alkyl group.

7. The rechargeable electrochemical cell as set forth in claim 1 wherein $R_4$ and $R_5$ are independently a $C_2$-$C_5$ alkyl group.

8. The rechargeable electrochemical cell as set forth in claim 1 wherein:
    $R_1$ and $R_2$ are independently an alkoxy group;
    at least one of $R_4$ and $R_5$ is an alkyl group, a haloalkyl group, an alkyl ether group, an acyl group, or a haloacyl group.

9. The rechargeable electrochemical cell as set forth in claim 1 wherein $R_4$ and $R_5$ are independently an alkyl group, an alkyl ether group, an acetyl group, and a trifluoromethyl group.

10. The rechargeable electrochemical cell as set forth in claim 1 wherein said active material is dissolved in the charge-carrying electrolyte.

11. The rechargeable electrochemical cell as set forth in claim 1 wherein said charge-carrying electrolyte comprise a co-solvent.

12. The rechargeable electrochemical cell as set forth in claim 1 wherein said active material has an oxidation potential of from 3.5 to 5V as compared to Li/Li$^+$.

13. The rechargeable electrochemical cell as set forth in claim 1 wherein said active material provides overcharge protection to said rechargeable lithium-ion cell after at least 10 charge-discharge cycles at a charging voltage sufficient to oxidize said redox shuttle and at an overcharge flow equivalent to 100% of cell capacity during each charge-discharge cycle.

14. The rechargeable electrochemical cell as set forth in claim 1 wherein said active material is present in an amount of from 1 to 10 percent by weight based on a total weight of said charge-carrying electrolyte.

15. The rechargeable electrochemical cell as set forth in claim 1 wherein the electrochemical cell is a lithium-ion cell and the active material is a redox shuttle.

16. The rechargeable electrochemical cell as set forth in claim 1 wherein the electrochemical cell is a redox flow battery and the active material is a catholyte material.

17. A rechargeable electrochemical cell comprising:
a positive electrode having a recharged potential;
a negative electrode;
a charge-carrying electrolyte; and
an active material having the following structure:

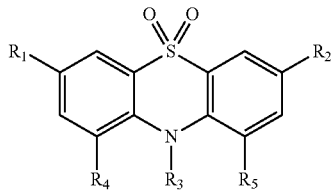

wherein:
$R_1$ and $R_2$ are independently an alkyl group, a nitrile group, a haloalkyl group, a perhaloalkyl group, an acyl group, an acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group;
$R_3$ is an an alkylaryl group, a trialkylammoniumalkyl group, a phosphate group, a phosphonate group, an alkyl phosphonate group, or a trialkylanilinium group; and
$R_4$ and $R_5$ are independently hydrogen, an alkyl group, a haloalkyl group, a perhaloalkyl group, an acyl group, an acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group,
wherein when one of $R_4$ and $R_5$ is a hydrogen atom, the other of $R_4$ and $R_5$ is not a hydrogen atom.

18. The rechargeable electrochemical cell as set forth in claim 17 wherein the electrochemical cell is a redox flow battery and the active material is a catholyte material.

19. A redox flow battery comprising:
a positive electrode;
a negative electrode;
a charge-carrying electrolyte; and
a catholyte material having the following structure:

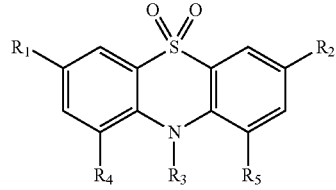

wherein:
$R_1$ and $R_2$ are independently an alkoxy group;
$R_3$ is an alkylaryl group, a trialkylammoniumalkyl group, a phosphate group, a phosphonate group, an alkyl phosphonate group, or a trialkylanilinium group; and
$R_4$ and $R_5$ are independently hydrogen, an alkyl group, a haloalkyl group, a perhaloalkyl group, an acyl group, an acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

* * * * *